(12) United States Patent
Polizopoulos et al.

(10) Patent No.: US 10,173,949 B2
(45) Date of Patent: Jan. 8, 2019

(54) OPTIMIZING AN ALKYLATION OLEFINS SOURCE

(71) Applicant: ExxonMobil Chemical Patents Inc., Baytown, TX (US)

(72) Inventors: Ipokratis Polizopoulos, Beaumont, TX (US); Ezra J. Czuba, Humble, TX (US); Brian C. Mayo, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 16/041,494

(22) Filed: Jul. 20, 2018

(65) Prior Publication Data

US 2018/0327333 A1 Nov. 15, 2018

Related U.S. Application Data

(62) Division of application No. 15/000,375, filed on Jan. 19, 2016, now Pat. No. 10,053,398.

(60) Provisional application No. 62/116,651, filed on Feb. 16, 2015.

(30) Foreign Application Priority Data

Apr. 3, 2015 (EP) .................................... 15248032

(51) Int. Cl.
*C07C 2/62* (2006.01)
*C07C 2/58* (2006.01)
*G06Q 30/02* (2012.01)
*B01J 19/24* (2006.01)
*C10G 29/20* (2006.01)

(52) U.S. Cl.
CPC ............... *C07C 2/58* (2013.01); *B01J 19/245* (2013.01); *C07C 2/62* (2013.01); *C10G 29/205* (2013.01); *G06Q 30/0206* (2013.01); *B01J 2219/00002* (2013.01); *B01J 2219/00049* (2013.01); *B01J 2219/24* (2013.01); *C10G 2300/1081* (2013.01); *C10G 2300/1092* (2013.01); *C10G 2300/201* (2013.01)

(58) Field of Classification Search
CPC ...................................................... C07C 2/62
USPC ........................................ 585/720, 731, 956
See application file for complete search history.

(56) References Cited

U.S. PATENT DOCUMENTS 5,750,818 A * 5/1998 Mehlberg .................. C07C 2/54
585/446

* cited by examiner

*Primary Examiner* — Thuan D Dang (57) ABSTRACT

Alkylate is produced by supplying iso-$C_{4+}$ hydrocarbon feed to an alkylation reactor, and by further selectively supplying to the alkylation reactor an olefin selected from the group consisting of refinery grade propylene (RGP) and polymer grade propylene (PGP), and combinations thereof. The olefin feed is controlled such that the proportion of PGP supplied through the olefin feed inlet exceeds that of RGP for a predetermined time interval, using a special purpose computer programmed to optimize the allocation of PGP between alkylation production and a commodity market in order to increase total net profit margin.

3 Claims, 5 Drawing Sheets

OPTIMIZING AN ALKYLATION OLEFINS SOURCE

CROSS REFERENCE TO RELATED APPLICATIONS

This application is a divisional application of U.S. patent application Ser. No. 15/000,375 filed Jan. 19, 2016, now allowed, which claims the benefit of priority to U.S. Provisional Patent Application Ser. No. 62/116,651, filed Feb. 16, 2015, and European Patent Application No. EP 15248032.3 filed Apr. 3, 2015, the disclosures of which are fully incorporated herein by reference.

FIELD

The invention relates to the optimization of an olefins source in an alkylation process.

BACKGROUND

An alkylation unit is commonly used in modem petroleum refining to react isobutane with a light olefins source (e.g., at least one of propylene and butylene) in the presence of a strong acid catalyst to form a branched $C_7$ or $C_8$ alkane generally referred to as alkylate. Alkylate is a desirable motor gasoline blending component because it has a low vapor pressure, a high octane content, and a low sulfur content.

One of the reactions taking place in the alkylation unit involves connecting light hydrocarbon molecules, e.g., connecting light olefin or isoolefin to isoalkane or isoalkene, such as connecting a $C_3$ olefin to a $C_4$ isoolefin or a $C_4$ isoalkane. Conventionally, the $C_3$ olefin is obtained from refining processes as a component of a gas mixture called refinery grade propylene ("RGP"). RGP comprises primarily $C_3$ olefin and propane. Since propane does not react in the alkylation unit, the alkylation process includes means for separating propane from the alkylate downstream of the alkylation unit.

The alkylation process does not require pure propylene or pure iso-$C_4$ hydrocarbon. Thus, it has heretofore not been considered desirable to concentrate the olefins source, e.g., by removing alkanes, before feeding the olefins to the alkylation unit. Rather, light olefins source streams are typically produced by a refinery in terms of "carbon-number purity". That is, $C_3$ hydrocarbons are collected in one stream and $C_4$ hydrocarbons are collected in a separate stream. A $C_3$ light olefins source stream can comprise about 60 wt. % propylene, with the remainder comprising mostly propane. An iso-$C_4$ hydrocarbon source stream can comprise $\geq 50$ wt. % iso-$C_4$ hydrocarbon, with $\geq 50$ wt. % of the remainder comprising butane, typically normal butane. One conventional process for producing alkylate is disclosed in Alkylation of Isobutane with Propylene, E. C. Oden and W. J. Burch, Industrial and Engineering Chemistry 41, 11, 2524-2529 (1949). The reference discloses producing alkylate by reacting olefin (propylene and/or butylene) with isobutane in the presence of a sulfuric acid catalyst. Unreacted vapors separated from the reactor's effluent are compressed in a refrigeration compressor and then recycled to the alkylation reactor. Isobutane and butane are separated from the liquid portion of reactor effluent. Light and heavy alkylates are conducted away. Propane present in the feed is recovered in a depropanizer stage. As disclosed in the reference, the depropanizer is integrated with both the refrigeration and alkylate-recovery stages.

It has been observed that the capacity of the alkylation unit can be limited by the amount of propane in the RGP feed. If the amount of propane was lessened and the amount of propylene was increased, the alkylation unit could make more alkylate. Thus, propane is a diluent that bottlenecks the alkylation unit. It is desired to at least partially overcome this bottleneck.

SUMMARY

It has been found that an alkylation unit's capacity can be increased by optimizing olefins sources available to the alkylation unit, which lessens the amount of propane in the olefin feed and increases the amount of propylene. More particularly, the aforementioned shortcomings of using RGP can be alleviated by using, as an input feed to the alkylation unit, a different grade of propylene which comprises nearly 100% propylene. This is called polymer grade propylene (PGP) because it is commonly used as a feed to make polymer. It has not been heretofore desirable to use PGP as a feed to an alkylation unit because using PGP to make polymer has historically been a much higher-value use than making alkylate, and, consequently, refineries have not been equipped to use PGP as an alkylation feed. However, the business environment has become more dynamic. There are times when gasoline prices are high, and propylene prices low, and vice versa. Thus, under certain conditions it becomes feasible to add PGP to the alkylation unit. Using PGP is advantageous because it does not contain propane, and thus the additional propane separation capacity, which is expensive to operate, is not needed. However, there are other times when gasoline prices are low and propylene prices are high, and thus using RGP is more desirable.

The invention is based in part on the development of a system that intelligently switches between PGP and RGP feeds to the alkylation unit. In certain aspects, the system is computer controlled and optimizes the olefin source to comprise PGP and RGP as variably selectable input feeds to the alkylation unit. These can be selected in the alternative, or blended, based on a control algorithm performed by the system.

Therefore, according to certain aspects, a method is provided for producing alkylate in an alkylation unit reactor having an iso-$C_{4+}$ hydrocarbon feed inlet, an olefin feed inlet and an alkylation catalyst inlet. Iso-$C_{4+}$ hydrocarbon is supplied to the iso-$C_{4+}$ hydrocarbon feed inlet of the alkylation unit reactor. Olefin is supplied to the olefin feed inlet in a way that allows a selected amount of PGP to be used to constitute at least a portion of the olefin feed. More specifically, RGP is supplied by a first system that is coupled (directly or indirectly) to the olefin feed inlet of the alkylation unit reactor, while PGP is supplied by a second system that is also coupled (directly or indirectly) to the olefin feed inlet of the alkylation unit reactor. The method controls the coupling of the first and second systems to the olefin feed inlet such that the amount of PGP supplied through the olefin feed inlet can be increased, e.g., to establish a flow of PGP to supplement or even exceed the flow of RGP to the alkylation unit for a predetermined time interval. Advantageously, since PGP is not a significant source of propane, adding PGP to the olefin feed generally does not result in a need for additional propane separation capacity. At least one alkylation catalyst, typically an acid catalyst, is supplied to the alkylation unit reactor via the alkylation catalyst inlet, allowing the iso-$C_{4+}$ hydrocarbon and olefin to react to produce alkylate.

According to further aspects, a method is provided for increasing alkylate production in an existing alkylation unit. The method comprises providing an existing hydrocarbon processing facility, the existing hydrocarbon processing facility comprising at least one alkylation unit and at least one propane separation stage located downstream of the alkylation unit. The alkylation unit is configured to produce an effluent comprising alkylate from propylene and a second hydrocarbon, the second hydrocarbon comprising at least one iso-$C_{4+}$ hydrocarbon. The propane separation stage is configured for removing propane from the alkylation unit's effluent. The method further includes configuring the existing hydrocarbon processing facility to supply at least one of RGP and PGP to the alkylation unit. The amount of RGP supplied to the alkylation unit is less than or equal to a maximum amount of propane separable by the propane separation stage. The amount of RGP supplied to the alkylation unit is supplemented with an amount of PGP.

In other aspects, a method is provided for optimizing PGP usage. The method comprises configuring an alkylation unit to produce alkylate from propylene and a second hydrocarbon, the second hydrocarbon comprising at least one iso-$C_{4+}$ hydrocarbon. One or more propylene sources is configured to supply RGP and PGP to the alkylation unit. The amount of PGP supplied to the alkylation unit is increased when the PGP is more valuable as a feed to the alkylation unit than it is as a commodity chemical. Accordingly, a first value is generated by producing a preselected alkylate amount from a preselected PGP amount in the alkylation unit, and a second value is generated by selling of the preselected PGP amount on a commodity market. The first and second values are compared, and the amount of PGP supplied to the alkylation unit is increased when the first value is greater than the second value.

DEFINITIONS

All words in this specification and appended claims are intended to have their conventional meaning. For further clarity, the conventional meaning of some terms is set forth below.

"Refinery grade propylene" (RGP) refers to an olefin comprising from about 50 wt. % to 70 wt. % propylene, with a majority of the remainder comprising propane. Typically, RGP has one or more of the following properties: (i) the RGP comprises 50 wt. % to 80 wt. % propylene, e.g., 55 wt. % to 75 wt. %, (ii) ≥90 wt. % of the remainder of the RGP comprising propane, e.g., ≥95 wt. %, and (iii) the RGP comprises ≤10 ppm by weight ("ppmw") of $C_4$ hydrocarbon, e.g., an amount of $C_4$ hydrocarbon in the range of 1 ppmw to 10 ppmw, based on the weight of the RGP.

"Polymer grade propylene" (PGP) refers to an olefin comprising from ≥90 wt. % propylene. Typically, PGP has one or more of the following properties: (i) the PGP comprises 95 wt. % to 100 wt. % propylene, e.g., 99 wt. % to 100 wt. %, (ii) ≥90 wt. % of any remainder of the PGP comprising propane, e.g., ≥95 wt. %, such as ≥99 wt. %, and (iii) the PGP comprises ≤1 ppmw of $C_4$ hydrocarbon, e.g., an amount of $C_4$ hydrocarbon in the range of 0.05 ppmw to 0.5 ppmw, based on the weight of the PGP. For example, the PGP can comprise ≤1.0 wt. % propane, e.g., ≤0.1 wt. %, such as ≤0.01 wt. %. The PGP can consist essentially of or even consist solely of propylene.

"Computer-readable medium" includes any medium or mechanism for storing or transmitting information in a non-transitory form readable by a computer. For example, a computer-readable medium includes, but is not limited to, read only memory ("ROM"), random access memory ("RAM"), magnetic disk storage media, optical storage media, and flash memory devices.

The term "$C_n$" hydrocarbon wherein n is a positive integer means hydrocarbon having n carbon atom(s) per molecule. The term "$C_{n+}$" hydrocarbon wherein n is a positive integer means hydrocarbon having at least n carbon atom(s) per molecule. The term "$C_{n-}$" hydrocarbon wherein n is a positive integer means hydrocarbon having no more than n carbon atom(s) per molecule. The term "hydrocarbon" means compounds containing hydrogen bound to carbon, and encompasses (i) saturated hydrocarbon, (ii) unsaturated hydrocarbon, and (iii) mixtures of hydrocarbons, including mixtures of hydrocarbons (saturated and/or unsaturated) having different values of n.

The term "iso-$C_{4+}$ hydrocarbon" means $C_{4+}$ hydrocarbon molecules having at least one tertiary carbon atom. When used as a feed to an alkylation unit, the iso-$C_{4+}$ hydrocarbon generally comprises ≥50 wt. % iso-$C_4$ hydrocarbon, e.g., 50 wt. % to 95 wt. % iso-$C_4$ hydrocarbon, such as 55 wt. % to 90 wt. % iso-$C_4$ hydrocarbon, with ≥90 wt. % of the remainder comprising normal $C_4$ hydrocarbon. Typically, the iso-$C_4$ hydrocarbon feed comprises ≥50 wt. % of isobutane, e.g., 50 wt. % to 99 wt. % isobutane, such as 80 wt. % to 98 wt. %, or 90 wt. % to 97 wt. %, with ≥90.0 wt. % of the remainder comprising normal butane, such as ≥99 wt. % normal butane. The isobutane feed to the alkylation unit is preferably substantially free of one or more of (i) butenes, including isobutene, (ii) $C_{5+}$ hydrocarbon, and (iii) $C_{3-}$ hydrocarbon. In this context, the term "substantially free" means the isobutene feed to the alkylation unit comprises ≤1.0 wt. % of the designated compounds, e.g., ≤0.1 wt. %, such as ≤0.01 wt. %, or ≤0.001 wt. %.

Description of Particular Aspects

Figure 1:
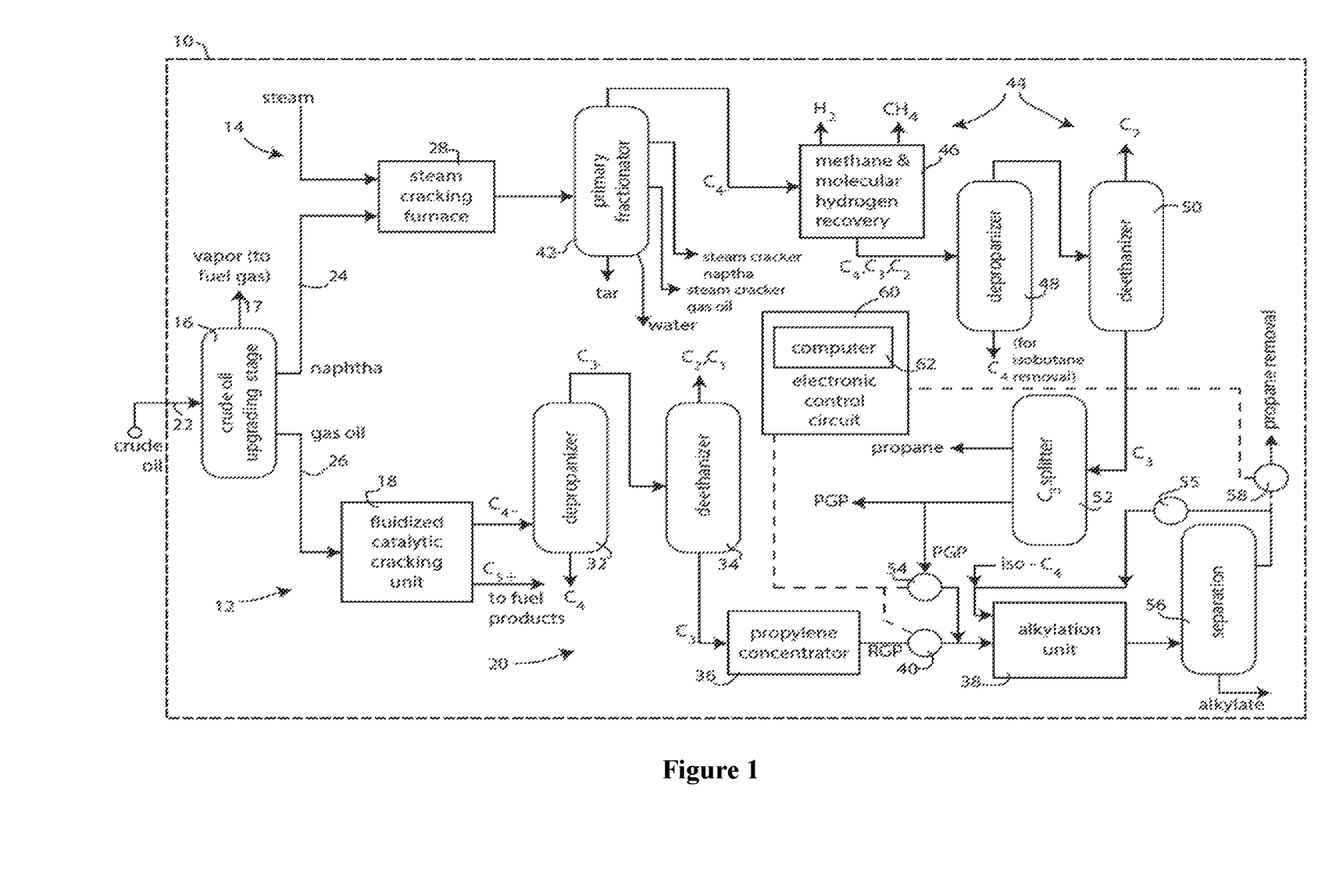
FIG. 1 is a schematic chemical process diagram depicting an exemplary hydrocarbon processing facility which utilizes the olefin optimizing techniques of the present disclosure.

Certain aspects of the invention will now be described with reference to FIG. 1. The invention is not limited to these aspects, and this description is not meant to foreclose other aspects within the broader scope of the invention. FIG. 1 diagrammatically illustrates a hydrocarbon processing facility enclosed by a fence or boundary 10. The facility includes a refinery section 12 and a chemical plant section 14 which are preferably co-located within the boundary 10. The refinery section includes a crude oil upgrading stage 16 (and any associated upgrading units such as light ends units and/or cokers), a fluidized catalytic cracking unit 18, and a cracked product recovery stage 20. Recovery stage 20 is configured to recover (i) $C_{5+}$ hydrocarbon, which are normally liquid at ambient temperature and pressure, and (ii) relatively low molecular weight molecules such as molecular hydrogen and $C_{4-}$ hydrocarbon, which are normally vapor at ambient temperature and pressure. The recovered $C_{5+}$ hydrocarbon can be conducted away, e.g., for use as fuel or fuel blendstock. Propylene can be separated from the recovered $C_{4-}$ hydrocarbon for use as RGP.

The hydrocarbon process facility of FIG. 1 utilizes crude oil as a hydrocarbon source. This is by way of illustration, and is not meant to foreclose other aspects within the broader scope of the invention, such as those utilizing a different hydrocarbon source, e.g., hydrocarbon that is not of geological origin. In accordance with the aspects illustrated in FIG. 1, crude oil is conveyed to the facility from outside the boundary 10, as at 22. The crude oil is upgraded in the upgrading stage 16, which typically includes at least two distillation towers: one, called an atmospheric pipestill, operates at atmospheric pressure and the second, called a vacuum pipestill, operates at less than atmospheric pressure. These two pipestills separate from the crude groups of hydrocarbon molecules having atmospheric boiling points in a specific temperature range (typically referred to as fractions). The residual portion of the crude oil that does not boil in either pipestill is typically conducted away, e.g., for deasphalting and coking of the deasphalted product to make coker naphtha and coker gas oil.

At least one vapor-phase fraction is typically conducted away from distillation towers. The separated vapor can comprise one or more of butanes, normal butenes, isobutene propane, propylene, ethane, ethylene, and methane. In this vapor stream, shown at 17, the olefin is present in very small concentration, if at all. These gases can be used, e.g., as fuel within the facility, or can be conducted away for storage and/or further processing. Alternatively, the vapor stream can be conducted to a "light end" unit for recovering useful gases (those having a higher value than fuel gas) such as isobutene and propylene. The light end unit can include catalytic conversion units, such as propane dehydrogenation units, for converting at least a portion of the vapor stream's propane to propylene. Although not shown in FIG. 1, the effluent of propane dehydrogenation (propane plus propylene) can be used as a source of refinery grade propylene (RGP).

The upgrading stage 16 typically provides two side streams: a naphtha stream 24 and a gas oil stream 26. The naphtha stream (called straight-run or virgin naphtha) can be used, as illustrated, as a feed to the chemical plant section 14 located at the facility. Although the octane number of virgin naphtha is typically too low to use "as-is" in gasoline blending, it can be utilized in the chemical plant section for as a steam cracker feed. Although the aspects illustrated in FIG. 1 utilize virgin naphtha as feed to steam cracker 28, the invention is not limited to steam crackers which use virgin naphtha as a feed or feed component. For example, coker naphtha can also be used as a steam cracker feed (not shown) instead of or in addition to virgin naphtha, as can $C_2$-$C_4$ hydrocarbon (e.g., butane, propane, and ethane obtained from a light ends unit (not shown)) crude oil, crude oil fractions, etc.

The gas oil stream 26, when obtained from the vacuum pipestill, is called a vacuum gas oil. The gas oil stream 26 is conducted to the fluidized catalytic cracking unit (FCCU) 18 located within the refinery section 12 of the facility. The FCCU 18 is primarily used to make $C_{5+}$ hydrocarbon, which can be used as fuel, such as gasoline and diesel, or components thereof. The FCCU also makes light gases such as molecular hydrogen and $C_4$ hydrocarbon. The $C_{4-}$ hydrocarbon typically contains much more olefin than does vapor stream 17. The $C_{4-}$ hydrocarbon obtained from the FCCU are typically processed through depropanizer 32, for separating $C_4$ and $C_{3-}$ hydrocarbon streams, and deethanizer 34, for separating $C_3$ and $C_{2-}$ hydrocarbon streams from the debutanizer effluent.

The mixed $C_3$ gases obtained from the deethanizer 50 potentially contain enough propylene to use as refinery grade propylene (RGP) without further upgrading. When they do not, a propylene concentrator 36 can be used to increase the propylene content to a concentration needed to produce RGP. The concentrator can do this, for example, in one or more stages for separating a portion of the propane from the propylene. Conventional propylene concentrators can be used, but the invention is not limited thereto. Separated propane is conducted away from the concentrator by one or more conduits, not shown.

A source of RGP, e.g., RGP obtained directly from stage 34's $C_3$ output or indirectly via propylene concentrator 36, is coupled to the alkylation plant (illustrated schematically as unit 38), preferably using valve means operating under the control of an electronic circuit, as will be discussed further below. Besides olefin feed, the alkylation unit receives a second feed comprising iso-$C_{4+}$ hydrocarbon, such as iso-$C_4$ hydrocarbon (isobutane and/or isobutene). It has been observed that the presence of isobutene during the alkylation reaction results in undesirably low-value products. To avoid this, the concentration of isobutane in the iso-$C_4$ feed is typically greater than the concentration of isobutene. In certain aspects, the iso-butane:isobutene molar ratio in the iso-$C_4$ olefin feed is $\geq 4$, e.g., $\geq 20$, such as $\geq 40$. The invention will now be described with respect to alkylation processes utilizing an iso-$C_{4+}$ hydrocarbon feed comprising isobutane. The invention is not limited to these aspects, and this description is not meant to foreclose other aspects within the broader scope of the invention, such as those featuring an iso-$C_{4+}$ hydrocarbon feed comprising isopentane and/or isopentene.

For the aspects illustrated in FIG. 1, the alkylation unit 38 catalytically reacts propylene in the olefin feed with isobutane feed to produce alkylate. The alkylation reaction typically includes reacting propylene with isobutane to produce an alkylate comprising primarily isoheptane, e.g., $\geq 10$ wt. % isoheptane, such as $\geq 25$ wt. %, or $\geq 50$ wt. %, or $\geq 75$ wt. %. The alkylation catalyst typically comprises a catalytically effective amount of acid, such as hydrofluoric acid and/or sulfuric acid. Alkylate has a boiling point at atmospheric pressure in the naphtha boiling range (e.g., 30° F. to 430° F.) and a very high octane number compared to certain naphthas produced by other petrochemical operations. These properties make alkylate particularly useful as a blendstock for producing high-octane gasoline. The isobutane for this process can be obtained, if desired, from a refinery recovery section and for a steam cracker recovery section described below.

Propylene does not typically react with other propylene molecules, so the total hydrocarbon feed to the alkylation unit (isobutane feed+olefin feed) typically contains more isobutane on a molar basis than propylene. Propane present in the olefin feed (e.g., when the olefin feed comprises RGP) does not typically react with isobutane under alkylation process conditions, so the propane is conducted away with the alkylate and/or unreacted isobutane.

Turning attention now to the chemical plant section 14, the steam cracking furnace 28 makes ethylene and propylene as its primary products, typically much more of these than is made by the FCCU 18. Steam cracker naphtha and steam cracker gas oil are separated from the steam cracker effluent, typically in the primary fractionator 42, and are conducted away. Vapor obtained from the primary fractionator is compressed in a compressor (not shown) and then sent to the steam cracker recovery stage 44. The vapor typically comprises molecular hydrogen, methane, ethane, ethylene, propane, propylene, and $C_4$ hydrocarbon. The steam cracker recovery stage typically includes at least one cryogenic separation stage, e.g., at least one cold box 46, for recovering from the vapor $C_{2+}$ hydrocarbon and a tail gas comprising primarily methane and molecular hydrogen. Depropanizer 48 is used for separating a $C_4$ stream to provide a stream comprising $C_2$ hydrocarbon and $C_3$ hydrocarbon. Iso-$C_4$ hydrocarbon, such as isobutane and/or isobutene can be obtained from the separated $C_4$ stream by conventional means. At least a portion of the separated isobutane stream can be transferred as iso-$C_4$ hydrocarbon feed to the alkylation unit. Deethanizer 50 is used for separating a $C_2$ stream from the $C_2+C_3$ effluent of stage 48. Ethylene can be recovered from the $C_2$ hydrocarbon, e.g., using a $C_2$ splitter (not shown). A deethanizer effluent, comprising mainly $C_3$ hydrocarbon, is conducted to a $C_3$ splitter 52 for recovering propane and propylene. The $C_3$ splitter is typically designed to produce polymer grade propylene (PGP), although one or more propylene concentrators can also be used if needed. Valve means, e.g., valve 54, can be utilized for coupling the PGP source to the olefin feed of alkylation unit 38. When valve 54 is set to a first state, PGP is conducted away, e.g., for polymerization and/or for sale as a commodity petrochemical. The polymerization can be located at or proximate to the facility, but this is not required. When valve 54 is set to a second state, at least a portion of the PGP is conducted as olefin feed to the alkylation unit 38, as will now be described.

By controlling the settings of valves 40 and 54, the system is able to use PGP in place of RGP in feeding the alkylation unit. In certain aspects, the valves 40 and 54 are configured to allow mixing of PGP and RGP in varying degrees to define the propylene feedstock to the alkylation unit. Whether configured in and either-or arrangement or a proportional mixing arrangement, these valves are preferably controlled by an electronic control circuit 60 that includes a special purpose computer 62 whose programming is discussed below. Use of PGP to feed the alkylation unit is signaled by the control circuit under at least two control conditions. First, PGP is used when it is cost-effective to do so. This may be determined by a calculation that takes into account (i) the energy used by the chemical plant section 14 needed to produce the PGP and/or (ii) the relative market values (current and/or predicted) of PGP as an alkylation feed and as a polymerization feed. For example, when polypropylene margins are low and alkylate margins are high, it can be cost effective to use the PGP to feed the alkylation unit.

In addition to the production cost and market value considerations, the computer-controlled electronic control circuit 60 can also take into account the throughput and propane waste product concentration of the alkylation unit, which varies depending on whether PGP has been introduced into the olefin feed stream. As discussed, the alkylation unit catalytically combines propylene with isobutane to produce the alkylate, which can then be used as a blendstock for making high octane gasoline. However, as discussed, propane does not react appreciably with the alkylation unit's olefin feed or feed under alkylation conditions. Consequently, when the alkylation unit's olefin feed comprises RGP, an appreciable amount of unreacted propane is typically conducted away from the alkylation unit. Thus as far as alkylate production is concerned, at least a portion of any unreacted propane in the alkylation unit's effluent is typically removed before the alkylate can be used as a gasoline blendstock. The presence of propane in the alkylation unit is a bottleneck that lessens alkylate production. PGP contains less propane than does RGP. Thus by introducing PGP into the feed stream of the alkylation unit, this bottleneck can be controlled or alleviated, thereby allowing greater propylene and/or isobutane flow to the alkylation unit, resulting in increased alkylate production without increasing the size of the alkylation unit.

Use of PGP as olefin feed to the alkylation unit improves alkylation unit efficiency for another reason as well. Effluent from the alkylation unit typically contains alkylate, propane and unreacted isobutane. A separation stage 56 is used for separating any unreacted propane and any unreacted isobutane from the alkylate. The separated propane is conducted away through valve 58, e.g., for use as fuel gas or a fuel gas component. The separated isobutane can be conducted away, but more typically is recycled to the alkylation unit to make more alkylate. Alkylation units utilizing RGP as the olefin feed typically produce an effluent that contains a significant amount of unreacted propane, resulting in a need for one or more propane separation stages having sufficient hydraulic capacity for efficient separation of unreacted propane from the alkylation unit's effluent. However, since PGP contains much less propane, the procedure for separating unreacted propane from the alkylation unit's effluent can be considerably simplified. For example, when the olefin feed to the alkylation unit comprises PGP, valve 58 can be maintained in a closed state, bypassing the propane removal mechanism and allowing any small amount of propane present in the separation stage to be fed back into the alkylation unit along with the unreacted isobutane. As the alkylation unit runs, this feedback of propane will cause the propane content in the isobutane recycle loop to gradually increase. When this residual propane increases in concentration to a sufficiently high level, e.g., to a pre-selected propane concentration in the isobutane recycle loop, the loop can be vented. For example, recycled isobutane and accumulated unreacted propane in the recycle loop can be conducted away, e.g., to a fuel gas storage unit, by opening valve 58 for a venting time period. The duration of venting time period can be pre-selected, e.g., based on the mass flow rate of recycle loop contents that are conducted away from the recycle loop via valve 58, in order to achieve a desired propane concentration in the recycle loop. Alternatively, or in addition, the duration of venting time period can be determined by (i) measuring or approximating the recycle loop's propane concentration $PC_i$, (ii) comparing that value to a predetermined propane concentration $PC_{ii}$, (iii) opening valve 58 to start the venting period when $PC_i$ exceeds $PC_{ii}$ by more than a first specified amount, and (iv) continuing the comparison of $PC_i$ and $PC_{ii}$ (discreetly, semi-continuously, or continuously) and closing valve 58 to end the venting time period when $PC_{ii}$ exceeds $PC_i$ by more than a second specified amount. Optionally, the first and second specified amounts, which trigger the start and end of the venting time period, are substantially equal. During the venting time period, additional isobutane can be obtained from the steam cracker recovery stage, or from another source, is substituted for the vented isobutane.

Figure 2:
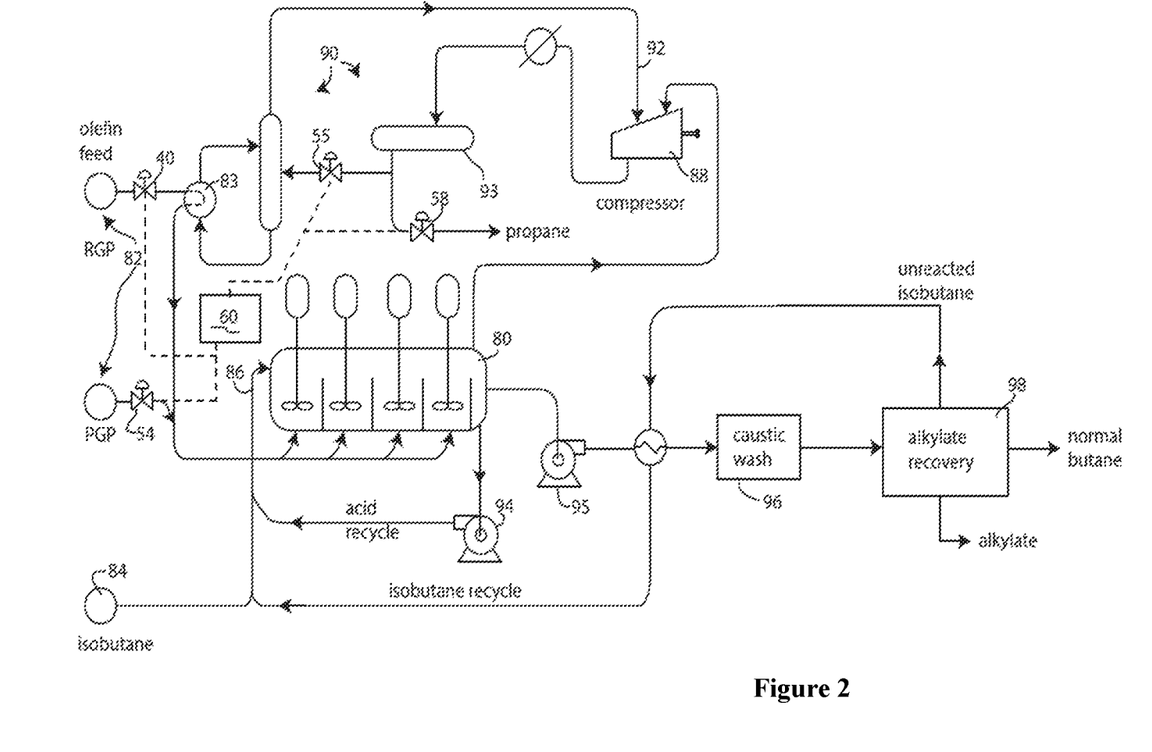
FIG. 2 is a schematic chemical process diagram depicting an exemplary alkylation unit or plant which utilizes the olefin optimizing techniques of the present disclosure.

Referring to FIG. 2, an exemplary alkylation unit has been shown, one that utilizes isobutane feed as the iso-$C_{4+}$ hydrocarbon feed and propylene as the olefin feed. In order to demonstrate the concepts and benefits of introducing PGP into the olefin feed stream, an auto-refrigeration alkylation unit implementing a sulfuric acid alkylation process has been depicted. It will be understood that the concepts of using PGP can also be applied in other types of alkylation units, such as those disclosed in the E. C. Oden and W. J. Burch reference cited in the BACKGROUND.

The auto-refrigeration process uses a multistage cascade reactor 80 with mixers in each stage to emulsify the mixture of alkylation catalyst (typically acid), propylene feed, and isobutane feed. The propylene feed 82 and isobutane feed 84 are introduced into the mixing compartments as shown. Specifically, acid catalyst and isobutane feed enter the first stage, as at 86, and pass in series through the remaining stages. The propylene feed is split and injected into each of the stages. As illustrated, the propylene feed 82 is configured to come from two alternately selectable sources, one providing RGP and one providing PGP. The PGP and RGP sources are coupled to the alkylation reactor's propylene feed, e.g., via valve means. The coupling is controlled, e.g., by adjusting the valve(s), to regulate the amounts of PGP and RGP in the propylene feed. For example, the amounts of PGP and RGP in the propylene feed are preferably regulated by valves 40 and 54, controlled by computer 60. The reactor typically operates at process conditions, e.g., flow rate, temperature, and pressure, to maintain the propylene feed, the isobutane feed, and the catalyst in the liquid phase at the start of the reaction. At least a portion of the heat from the alkylation reaction vaporizes at least a portion of the propylene feed and/or a portion of the isobutane feed. Vaporized feed is conducted away from the reactor to refrigerant compressor 88, for re-compression and re-use as refrigerant. One or more components of the propylene feed (e.g., PGP and/or RGP) can be cooled against re-compressed propane refrigerant, as shown.

More specifically, propane and/or isobutane that are vaporized to remove the heats of reaction and mixing energy are fed to compressor 88 where they are compressed and liquefied. A portion of this liquid is vaporized in economizer 90, to cool the olefin feed before it is fed to the reactor 80. Economizer 90 is typically located within alkylate separation stage 58 of FIG. 1. Vapors are returned as at 92 to the compressor for recompression. As illustrated, the remainder of the liquefied hydrocarbon is sent to a depropanizer column 93 for removal of any excess propane that accumulates in the system by opening valve 58 and closing valve 55 for the specified venting time period. Liquid isobutane from the bottom of the depropanizer is pumped (not shown) to the first stage of the reactor. The alkylation reaction is typically carried out with excess isobutane, and in certain aspects substantially all of the propylene present in the olefin feed is converted to alkylate. In these aspects, the vaporized reactants conducted to refrigeration compressor 88 comprise vaporized isobutane and vaporized propane (when the olefin feed comprises RGP). The process can be considerably simplified when the olefin feed comprises PGP. Since PGP contains little if any propane, there is little if any additional propane load on economizer 90 (particularly on depropanizer 93) when PGP is added to an RGP feed. When the propylene feed comprises a significant amount of PGP, e.g., ≥50 wt. %, such as 75 wt. %, based on the weight of the propylene feed, economizer 90 is typically not needed. In other words, depropanizing is typically not needed downstream of refrigeration compressor 88 when the olefin feed comprises PGP because (i) substantially all of the PGP's propylene is consumed in the alkylation reaction and (ii) PGP contains little if any propane, which would otherwise be vaporized by the alkylation reaction. This aspect of the invention enables operation with depropanizer 93 taken off-line, e.g., for maintenance, without taking the alkylation unit off-line. When depropanizer 93 is not used, valve 58 is utilized to lessen the amount of any accumulated propane in the liquid downstream of compressor 88. Alternatively or in addition, valve means can be used for this function upstream of refrigeration compressor 88.

The acid-hydrocarbon effluent from the last reactor stage is separated into acid and hydrocarbon phases, e.g., in a settler. The acid is removed for reclamation as at 94. The hydrocarbon phase is exposed to at least one caustic wash 96. After removing in stage 96 at least a portion of any acid, the hydrocarbon phase is fed to an alkylate recovery stage 98 for separating alkylate from the hydrocarbon phase. Alkylate recovery stage 98 is typically located within alkylate separation stage 58 of FIG. 1. Any normal butane separated in the alkylate recovery stage is typically conducted away. Unreacted isobutane is typically separated from the hydrocarbon phase and recycled to the alkylation reactor with fresh isobutane feed.

As shown in FIG. 2, the alkylation process can be operated cyclically, e.g., with (i) vaporized isobutane recompressed in the refrigerator compressor and recycled from the economizer as feed to the alkylation unit and (ii) unreacted isobutane in the liquid hydrocarbon portion of the alkylation reactor effluent recycled from the alkylate recovery section for use as feed to the alkylation unit. Any species in the propylene feed and/or isobutane feed that do not react in the alkylation process can gradually increase in concentration in recycle loops (i) and/or (ii). This includes both inert compounds that do not react, as well as detrimental compounds that do react but produce undesirable low value products. Since compounds such as propane and normal butane do not have a tertiary carbon atom, they do not react appreciably to produce alkylate. Isobutene, as discussed above, can react (e.g., with itself) to yield undesired products. This suggests that from a typical input mixture of normal butane, normal butene, propane, propylene, iso-butene, and isobutane, the isobutane content needs to be kept in sufficiently high concentration to allow the alkylation reaction to efficiently proceed. To achieve this, the process typically recycles the isobutane, while removing at least a portion of one or more of (i) any normal butane, (ii) any normal butene, (iii) any isobutene, and (iv) any propane present in the effluent (liquid phase and/or vapor phase) of the alkylation reactor.

The invention can be carried out using conventional alkylation process conditions. Suitable process conditions are disclosed in the E. C. Oden and W. J. Burch reference, which is cited in the BACKGROUND and is incorporated by reference herein in its entirety. Typical alkylation process conditions include, e.g., exposing the combines olefin feed and iso-$C_{4+}$ hydrocarbon feed to a temperature in the range of from 1° C. to 40° C. at a pressure in the range of from 102 kPa to 1035 kPa. The alkylation catalyst typically comprises acid, such as sulfuric acid and/or hydrofluoric acid. The catalyst typically comprises ≥85% by weight of the acid, based on the weight of the catalyst, with ≥90 wt. % of the balance of the catalyst comprising water and one or more acid-soluble oils. Spent acid can be removed from an outlet of the alkylation reactor. When the acid catalyst comprises sulfuric acid, spent sulfuric acid is replaced by adding concentrated sulfuric acid (typically ≥98 wt. % sulfuric acid) at an acid inlet to the alkylation reactor. When the acid catalyst comprises hydrofluoric acid, concentrated hydrofluoric acid (typically in the range of 85 wt. % to 95 wt. % hydrofluoric acid) is added at the catalyst inlet. The catalyst, olefin feed, and iso-$C_{4+}$ hydrocarbon feed typically subsist as an emulsion during the alkylation reaction, wherein the hydrocarbon is generally dispersed in a continuous acid catalyst phase. Typically, the emulsion comprises ≥40% by volume of the acid, based on the volume of the emulsion, e.g., ≥50%, such as in the range of 40% to 70% or 45% to 65%. When (i) the olefin feed comprises propylene and (ii) the iso-$C_{4+}$ hydrocarbon feed comprises isobutane, the isobutane:propylene molar ratio is typically in the range of from 5 to 10. Propylene space velocity (LHSV=[volume of propylene in the reactor per volume of catalyst in the reactor] per hour) is typically in the range of 0.2 $hr^{-1}$ to 0.7 $hr^{-1}$, such as 0.25 $hr^{-1}$ to 0.5 $hr^{-1}$. The invention is compatible with commercial-scale alkylate manufacturing facilities, e.g., those producing ≥10 $m^3$/hr of liquid alkylate, such as ≥100 $m^3$/hr/hour, including those producing ≥$10^3$ barrels of alkylate per day (about 160 $m^3$/day), such as in the range of $10^3$ barrels per day to $5\times10^4$ barrels per day (1600 $m^3$/day).

In the instant process, PGP is a preferred olefin feed. Because PGP contains little if any propane, the alkylation process is able to operate continuously for relatively long time periods, depending, e.g., on the amount of propane in the PGP, before it becomes desirable to bleed off the accumulated traces of propane. On the other hand, when RGP is used as the olefin feed, a significant amount of propane is introduced, typically resulting in a need to continually remove propane from one or more recycle loops. While it is possible to employ propane removal equipment downstream of the alkylation unit, such equipment would need to employ a separation facility to separate the propane from the desired isobutane reactant, e.g., economizer 90 in FIG. 2. When the olefin feed comprises propane (as it would be when RGP is used), the downstream equipment is typically of sufficient hydraulic capacity for handling the relatively large fluid flow rates resulting from the presence of propane in one or more of the recycle loops. Thus, the downstream propane removal process acts as a bottleneck that impedes maximum throughput of the alkylation unit.

In contrast, when PGP serves as the olefin feed, the system can be configured to periodically purge the propane downstream of the alkylation unit by opening a valve (e.g., valve 58 of FIGS. 1 and 2) to bleed off the unreacted propane along with any recycled isobutane accompanying the unreacted propane. While this will result in a small loss of isobutane available for immediate recycling, the lost isobutane can be obtained from the propane in an off-line process that does not impede the maximum throughput of the alkylation unit.

In certain aspects, PGP is obtained from commercial sources, e.g., a source external to the hydrocarbon processing facility (i.e., not within the boundary 10 shown in FIG. 1). In certain preferred aspects, the PGP generating facility producing the highly refined propylene is co-located at the same hydrocarbon processing facility with the alkylation unit designed to consume that propylene (i.e., both are within the boundary 10 of FIG. 1). Moreover, in these aspects, the co-located components are fluidically coupled (e.g., in direct fluid communication, such as via valves and conduits, with no intervening process equipment) so that at least a portion of the output of the PGP generating facility directly feeds the alkylation unit. In this configuration, because these two fluidically coupled units are working on concert, a computer-controlled electronic control circuit can be employed to keep the throughput of these two units optimized, particularly when a PGP generating facility and an alkylation unit are located proximate to one another within the hydrocarbon processing facility.

Special Purpose Computer

A computer-controlled electronic control circuit will now be described with particular reference to FIGS. 3*a*, 3*b*, 4 and 5. The electronic control circuit 60 (introduced above in connection with FIG. 1) preferably comprises a collection of electronically controlled sensors and actuators as well as a computer 62, which may be implemented by a single computer or by a system of interconnected computers (e.g., networked computers). Preferably the computer 62 has network connectivity to allow it to obtain market data used in the control algorithm. The control algorithm makes a determination of whether to use RGP or PGP (or optionally a blend of the two) as the feed to the alkylation unit. The algorithm takes into consideration a number of measured and externally obtained data.

Figure 4:
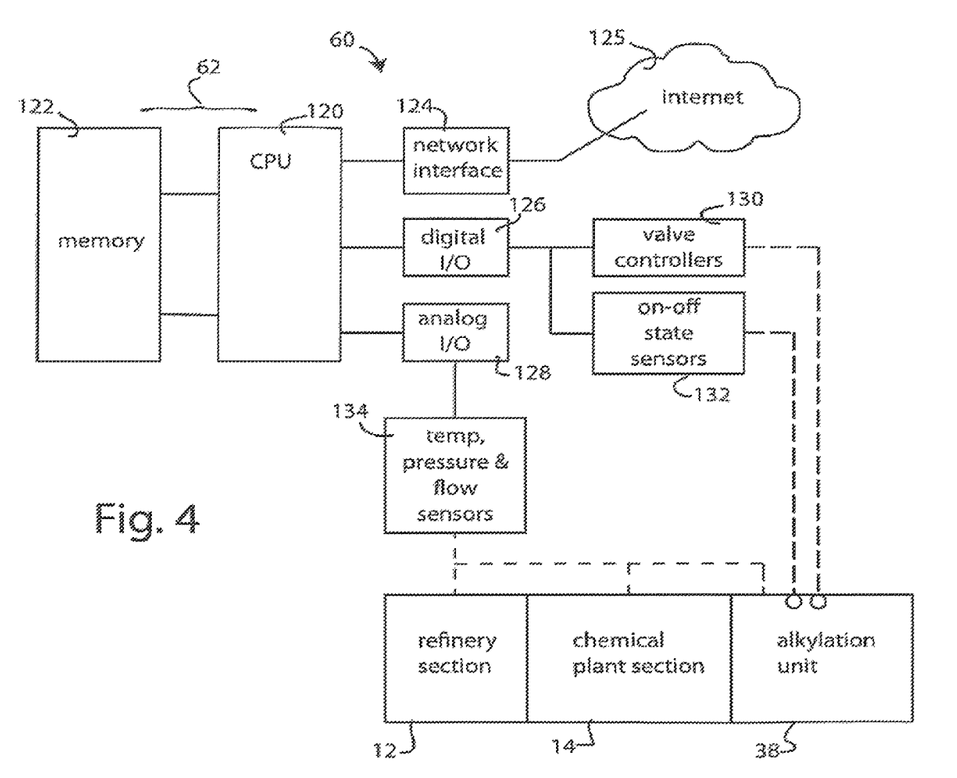
FIG. 4 is an electronic circuit diagram depicting an exemplary special purpose computer programmed to optimize the use of olefins by the alkylation unit.

Referring to FIG. 4, the electronic control circuit 60, including special purpose computer 62, may be implemented by one or more processors (CPU) 120 having associated random access memory 122 attached. The random access memory serves two purposes: it stores the executable instructions that the CPU 120 operates upon to implement the algorithms described below; and it stores data operated upon by those algorithms. Attached to computer 62 is a network interface circuit 124 that provides network connectivity with data sources, such as data sources available on the internet 125. As will be described, the CPU obtains market data from the internet using this network interface. The computer 62 is also provided with a digital input/output (I/O) port 126 and an analog input/output (I/O) port 128.

The digital I/O port 126 serves as the data transmitting and receiving port by which the CPU 120 sends logic control signals to the electronic valve controllers 130 and also receives on-off state information from digital on-off state sensors 132. As illustrated diagrammatically, these digital input and output connections communicate with the alkylation unit 38. Specifically, the valve controllers 130 provide control signals to operate the valves 40, 54 and 58. The on-off state sensors likewise attach to these valves and provide feedback signals reporting the actual states of each valve. Feedback is provided to ensure that the actual valve state matches what the logic control signal from the CPU has called for.

The analog I/O port 128 serves as the data receiving port by which the CPU 120 receives analog chemical process information from the refinery section 12, the chemical plant section 14 and the alkylation unit 38. These data may include flow rates, temperatures, pressures, chemical concentration readings, and the like. These analog data factor into the determination by the special purpose computer 62 of one or more of past values (e.g., recorded values), present values (e.g., substantially instantaneous values), future values (e.g., predicted values), accumulated values, and statistical (e.g. median, mean, and/or average) values used in determining when and how PGP should be introduced into the alkylation unit, and when certain purge or venting operations are performed (e.g., the start and/or end of the venting time period).

Figure 3A:
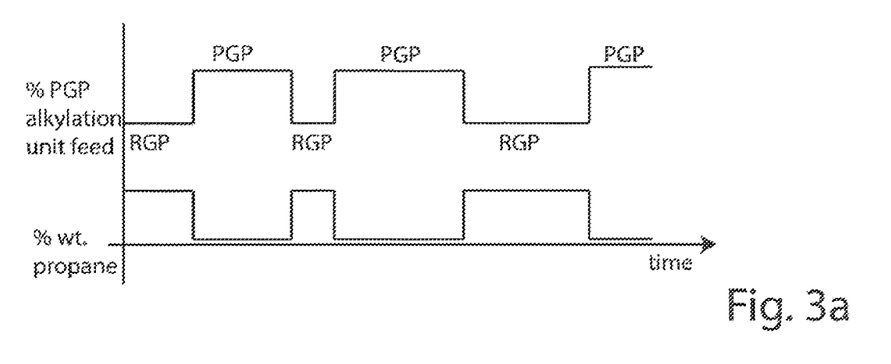
FIG. 3a is graph of percentage PGP and percentage of propane as a function of time, illustrating a first control system aspect.

In certain aspects, the control circuit effects control over the duty cycle by which RGP and PGP are fed to the alkylation unit. This duty cycle control is shown in FIG. 3*a*. As seen, the control circuit cycles between feeding RGP and PGP to the alkylation unit. The feed is cycled between RGP and PGP based on real time data captured from chemical processes within the petrochemical plant and/or based on one or more variables external to the alkylation unit, e.g., externally-obtained commodity market data. The control circuit uses a computer-implemented algorithm to selectively switch valves 40 and 54 (of FIGS. 1 and 2) between respectively alternating ON-OFF states to effect the variable duty cycle feed exemplified by FIG. 3a. In the variable duty cycle aspects, valves 40 and 54 are switched to fully open when ON and fully closed when OFF. Under control of the control algorithm, when one valve is switched ON, the other is switched OFF. Thus there is no real time blending of the respective RGP and PGP feeds. This results in an olefin feed to the alkylation unit that has a propane content that cycles between about 0% to 5% propane (when PGP is fed) and between about 30% to 50% propane (when RGP is fed).

Figure 3B:
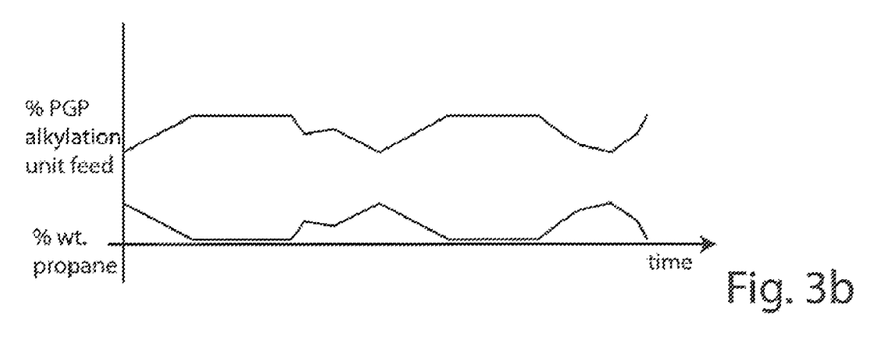
FIG. 3b is graph of percentage PGP and percentage of propane as a function of time, illustrating a second control system aspect.

In other aspects, shown in FIG. 3b, the valves 40 and 54 permit intermediate flow states to allow mixing of RGP and PGP in a variable ratio. If desired valves 40 and 54 can be configured as a single means, e.g., one mixing valve device that takes both RGP and PGP feeds as inputs and outputs a blended mixture of the two inputs depending on the variable position setting of the mixing valve device. The mixing valve aspects result in an olefin feed to the alkylation unit that has a varying propane content ranging from about 0% to 5% propane (at the one extreme) to about 30% to 50% propane (at the other extreme) and all ranges in between, depending on the valve setting.

The computer 62 performs the control algorithm and then sends control signals to the valves 40 and 54 based on the calculated results. In certain aspects the control algorithm runs continuously, so that the valve settings are adjusted in real time. In other aspects, the control algorithm runs under the mediating control of a control loop, which causes the valve settings to periodically change based on measurements derived from one or more of past measurements (e.g., recorded measurements), present measurements (e.g., substantially instantaneous measurements), future measurements (e.g., predicted measurements), accumulated measurements, and statistical (e.g., median, mean, and/or average) measurements. The mediating control loop may be set by adjusting a control parameter that establishes a loop cycle time of, for example, 24 hours. This would cause the valves settings to be adjusted once every 24 hours, if the measured values and attendant calculations so dictate.

More specifically in one preferred control algorithm, the respective instantaneous or statistical values of PGP and RPG are calculated and used along with the respective instantaneous or statistical production costs to determine the PGP vs RPG feed strategy for the alkylation unit. To determine the instantaneous or statistical values of PGP and RPG, the computer 62 is programmed to obtain one or more variables that are external to the alkylation unit, e.g., commodity market data indicating the value of PGP on one or more commodity markets. These data may be obtained via Internet real-time commodity data sources, such as ICIS, Houston, Tex. In addition, the computer 62 is programmed to obtain commodity market data indicating the value of PGP for use as an input the alkylation unit. In this regard, the alkylate produced by the alkylation unit is typically blended with fuel products produced by the cracking unit 18 (FIG. 1) to produce higher octane gasoline products. Thus the market data indicating the value of PGP as an alkylation unit feed will depend on the real time and/or statistical ratio, and respective selling prices, of regular grade gasoline vs higher octane blends. These data can be obtained via internet commodity data sources available from U.S. Energy Information Administration, http://eia.gov.

In addition to obtaining commodity market data reflecting the value of PGP as a commodity used in, for example, plastics production, vs as a feedstock for the alkylation process, the computer 62 also obtains data reflective of the cost to produce both RGP and PGP. These are preferably determined using sensors deployed within the plant, to monitor the energy and raw materials consumed in producing these two propylene products. Once these values are computed, the computer 62 derives an incremental value that reflects the additional cost of using PGP as an alkylation feed instead of RGP. However, as discussed above, PGP offers the benefit over RGP of greatly reducing the downstream burden of removing recycled propane from the alkylation unit output. Specifically, when PGP is used, the small quantity of extant propane can be periodically vented by opening valve 58. When this is done, a small quantity of desirable iso-$C_4$ hydrocarbon (particularly isobutane) is also vented. Because valve 58 is controlled by the electronic control circuit 60 and computer 62, this venting of iso-$C_4$ hydrocarbon is recorded and the amount vented is captured as data that may be used to more adjust the incremental value reflecting the additional cost of using PGP, if greater process control accuracy is desired.

With the PGP commodity market data and the PGP incremental cost data derived from actual plant operation, computer 62 then calculates valve control parameters that are used to electronically control valves 40 and 54, and also purge valve 58 if implemented.

Figure 5:
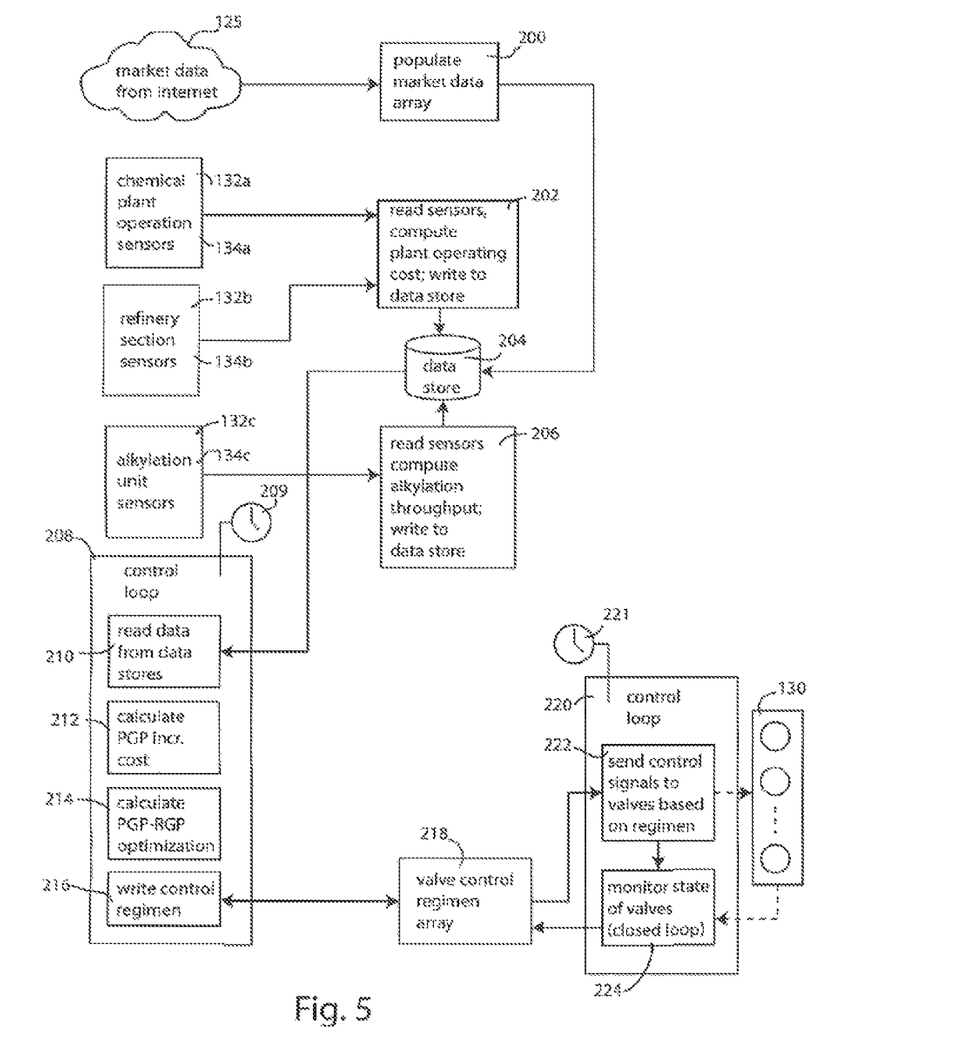
FIG. 5 is a flow diagram illustrating the manner of programming the processor (CPU) of the special purpose computer.

By way of example, FIG. 5 shows a control algorithm that may be executed by the CPU 120 of the special purpose computer 62. This illustrated example performs many tasks asynchronously, gathering data when appropriate, but using that data under a different control cycle that may or may not be in synchronism with the data gathering. Thus, as illustrated at step 200, the CPU accesses the internet 125 to download market data and store that data in an array data structure maintained within memory 122 of FIG. 4. This can be done periodically at a rate sufficient to maintain current market data in the array. As illustrated, the array may be stored in association with date and timestamp information in data store 204, making the obtained values available for further computations in determining the optimal valve control regimen.

Meanwhile as at step 202, the CPU 120 of FIG. 4 reads the analog and digital sensors and stores the obtained readings in an array data structure within memory 122. The CPU then uses the stored data readings to perform a computation to assign a plant operating cost and then writes this operating cost data, e.g., to the data store 204. For example, the sensor readings may be stored in the array data structure, organized by the time at which each reading was taken. The CPU then processes these readings, correlating those within common timeframes, and computing aggregate or statistical values (e.g., median values, average values, etc.). The operating cost data in data store 204 thus represents an aggregate value, which is in turn based on many analog and digital readings taken over a period of time as the plant operates.

Similarly, at step 206 the CPU 120 reads the analog and digital sensors from the alkylation unit 38 and stores its state data, e.g., to the data store 204. As seen, it is not necessary that the data store values of the alkylation unit be generated at the same rate as those from the chemical plant and refinery sections. Rather the data for one of these respective subsystems can be gathered at the rate appropriate for it.

The CPU 120 computes a valve control regimen that is ultimately used to control the valves governing use of PGP within the alkylation unit. In the illustrated aspects the CPU performs a control loop 208, at a cycle rate dictated by timer 209. Each time the CPU executes control loop 208, the following steps are performed. Data are read from data store 204, as at step 210. The CPU then calculates at step 212 the PGP incremental cost, reflecting the overall excess cost of using PGP instead of, or in addition to RGP. The CPU then, at step 214, performs a PGP-RGP optimization that seeks the optimal PGP utilization amount, based on the PGP incremental cost and based on market data obtained from the market data array 200, and stored in data store 204. Once this optimal PGP utilization amount is calculated, the CPU uses that value to write data to a valve control regimen stored in an array within memory as at 218. If desired, this regimen can include several different PGP utilization settings, to be used at future times or in response to future events within the plant. Thus the valve control regimen is effectively a PGP to-do list, that instructs the plant when PGP should be introduced into the alkylation unit and under what constraints (such as whether RGP should also be introduced and in what ratio).

The CPU 120 performs actual control of the valve controllers 130 for the alkylation unit in a second control loop 220, at a cycle rate dictated by timer 221. Following this control loop, the CPU at step 222 reads the valve setting values from the valve control regimen array, selects the value appropriate for the current date and time and then sends logic control signals to the valve controllers 130, which in turn cause the valves 40, 54 and 58 to operate as required by the regimen. The control loop 220 includes step 224 that reads the current states of the controlled valves and feeds this information back to the valve control regimen. By recording into the control regimen array the current valve state in association with the state called for by the regimen, the CPU can use this information to feed back to the algorithm at 216 which generates the control regimen. In this way, the control regimen can be adaptively adjusted based on actual alkylation unit performance. The valve states are also compared in step 224 to ensure that the states called for by the control regimen are actually being performed. If not, remedial action can be signaled. Similarly, operation of economizer 90 in FIG. 2 (typically used when RGP is present in the olefin feed) can also be regulated by operating valves 55 and 56, e.g., under the control of electronic control circuit 60 and/or the control of a second control circuit. In aspects where an economizer is not used, the amount of propane present in the recycled vapor effluent of reactor 80 can also be regulated by operating valves 55 and 56, e.g., under the control of electronic control circuit 60 and/or the control of a third control circuit.

Certain aspects and features have been described using a set of numerical upper limits and a set of numerical lower limits. It should be appreciated that ranges from any lower limit to any upper limit are contemplated unless otherwise indicated. Certain lower limits, upper limits, and ranges appear in one or more claims below. All numerical values are "about" or "approximately" the indicated value, and take into account experimental error and variations that would be expected by a person having ordinary skill in the art.

To the extent a term used in a claim is not defined above, it should be given the broadest definition persons in the pertinent art have given that term as reflected in at least one printed publication or issued patent. Furthermore, all patents, test procedures, and other documents cited in this application are fully incorporated by reference to the extent such disclosure is not inconsistent with this application and for all jurisdictions in which such incorporation is permitted.

While the foregoing is directed to aspects of the invention, other and further aspects of the invention may be devised without departing from the basic scope thereof, and the scope thereof is determined by the claims that follow.

What is claimed is:

1. A method of optimizing PGP usage, comprising:
configuring an alkylation unit to produce an effluent comprising alkylate, the alkylate being produced by reacting propylene with a second hydrocarbon, the second hydrocarbon comprising at least one iso-C4+ hydrocarbon;
configuring a propylene source to supply RGP and a propylene source to supply PGP to the alkylation unit;
determining a first market value, the first market value being generated by producing a preselected alkylate amount from a preselected PGP amount in the alkylation unit;
determining a second market value, the second market value being generated by selling of the preselected PGP amount on a commodity market;
comparing the first and second market values; and
during the process (i) increasing the PGP supply to the alkylation unit when the first market value is greater than the second market value; (ii) decreasing the PGP supply to the alkylation unit when the first market value is less than the second market value and (iii) maintaining substantially constant the PGP supply to the alkylation unit when the first market value is substantially equal to the second value.

2. The method of claim 1, wherein (a) the iso-$C_{4+}$ hydrocarbon comprises isobutane, (b) the PGP comprises ≤1.0 wt. % propane, and (c) unreacted isobutane is separated from the effluent and recycled to the alkylation unit for additional alkylation without separating additional propane from the unreacted isobutane during the increased PGP supply.

3. The method of claim 1, further comprising polymerizing at least a first portion of the PGP supplied by at least one of the propylene sources and producing at least a portion of the alkylate from a second portion.

* * * * *